United States Patent [19]

Singer

[11] Patent Number: 5,147,308

[45] Date of Patent: Sep. 15, 1992

[54] SURGICAL NEEDLE AND STYLET WITH A GUARD

[76] Inventor: Andrew Singer, 33 Pond Ave. Apt. 421, Brookline, Mass. 02146

[21] Appl. No.: 461,024

[22] Filed: Jan. 4, 1990

[51] Int. Cl.$^5$ ............................................. A61M 5/00
[52] U.S. Cl. .................................. 604/117; 604/164; 604/263; 128/754
[58] Field of Search ............... 604/117, 162, 164, 192, 604/198, 263; 128/754

[56] References Cited

U.S. PATENT DOCUMENTS

| | | | |
|---|---|---|---|
| 2,091,438 | 8/1937 | Epstein | 604/117 |
| 3,658,061 | 4/1972 | Hall | 128/214.4 |
| 4,142,517 | 3/1979 | Stavropoulos et al. | 128/2 B |
| 4,266,543 | 5/1981 | Blum | 604/263 |
| 4,378,810 | 4/1983 | Ishizaki et al. | 128/754 |
| 4,573,975 | 3/1986 | Frist et al. | 604/192 |
| 4,623,336 | 11/1986 | Pedicano et al. | 604/192 |
| 4,629,453 | 12/1986 | Cooper | 604/192 |
| 4,654,034 | 3/1987 | Masters et al. | 604/192 |
| 4,738,663 | 4/1988 | Bogan | 604/198 |
| 4,740,204 | 4/1988 | Masters et al. | 604/192 |
| 4,747,835 | 5/1988 | Sandhaus | 604/192 |
| 4,755,170 | 7/1988 | Golden | 604/198 |
| 4,917,672 | 4/1990 | Terndrup et al. | 604/198 |
| 4,966,582 | 10/1990 | Sit et al. | 604/263 |

FOREIGN PATENT DOCUMENTS

| | | | |
|---|---|---|---|
| 0949943 | 10/1949 | France | 604/117 |
| 2586568 | 3/1987 | France | 604/263 |
| 2620340 | 3/1989 | France | 504/192 |

OTHER PUBLICATIONS

Product literature, INRAD "Accumark Sheath".
Product literature, Monoject "ABC", Needle.
Product literature, Medi-tech "AIM" Movable Marker.

*Primary Examiner*—John D. Yasko
*Assistant Examiner*—Anthony Gutowski
*Attorney, Agent, or Firm*—Rines and Rines

[57] ABSTRACT

A rigid puncture-proof sterilizable shield or guard device and method of use for stylet-type stainless steel needles, functioning preferably in two ways: 1) to protect the user from inadvertent needle sticks when placing the stylet back in the needle hub, and 2) to serve as a needle depth guide insuring exact placement of the needle into the desired body space. Adjustable and fixed or nonmovable versions of the guard may be made preferably as a flared, conical member available at the hub to prevent inadvertent needle sticks.

2 Claims, 4 Drawing Sheets

SURGICAL NEEDLE AND STYLET WITH A GUARD

The present invention relates to surgical methods of probing the body with needles adapted to aspirate fluids or withdraw tissue and the like from desired locations in the body, and to improved apparatus for carrying out the same; being more particularly directed to needle-stylet structures in which the stylet occludes the needle lumen down to the distal insertion end opening during insertion into the body and is then removed to permit the attachment of, for example, syringes and the like as for the purpose of effecting fluid or tissue aspiration through the open needle lumen.

While the invention will illustratively first be described in connection with such fluid aspiration and biopsy or other tissue withdrawal modes of operation, it will be evident that the same needle-stylet apparatus is also used for the introduction of fluids, air and other gases, drugs and other materials to desired locations in the body, as for diagnostic or therapeutic intervention and similar purposes, as well.

For such and related purposes, sterile needle-stylet units are commonly injected or inserted into many parts of the body including vessels such as arteries and veins; joint spaces as for therapy and diagnosis in knees, hips, ankles, spine, discs, shoulders, etc.; the spinal canal; hollow and solid organs; tumors; abscesses; pericardial (heart), pleural (lung) and perinephric (kidney) spaces; amniotic fluid, umbilical cord and parts of the fetus in connection with pregnant women; lymph channels; brain ventricles, and the vitreous of the eye, to mention some of the more common.

Despite the wide-spread universal use of needle aspiration, drainage, biopsy, space access, localization, ablation and injection, the problem underlying the present invention residing in the danger of sticking the fingers of the physician or nurse in the often frequent reinserting of the stylet into the needle, as later more fully explained, has remained largely without solution; and unfortunately currently leaves the profession dangerously exposed to the ever-increasing threats of infection by AIDS, virus, hepatitis and other innoculum that may be present on the stylet after its contact with the patient.

The fundamental problem of inserting a stylet type needle into a defined or desired location within the body resides in the lack of knowledge as to whether the needle tip is actually in precisely the desired location. To be certain of correct needle placement, as hereinafter discussed, it is often necessary periodically to remove and then replace the stylet respectively from and into the needle for checking for correct placement. Because, however, of the very small size of the needle hub and the long length of the stylet, it is often difficult to replace the stylet back into the needle without risking an accidental puncture wound or sticking of the forefinger or other parts of the operator's hand holding the needle shank — it being impractical, both from a time and cost point of view, to replace the once-removed stylet with a new sterile stylet for each reinsertion.

While the art is replete with devices for protection in disposing of used needles themselves (as, for example, in U.S. Pat. Nos. 3,658,061; 4,738,663; 4,747,835 and 7; 4,573,975; 4,629,453; 4,623,336; 4,654,034 and 4,740,204), to applicant's knowledge there is no device available which can be used during the stylet reinsertion and removal procedure and during needle insertion in the body to prevent stylet wound types of injury; and certainly the different needle disposal techniques of the above-cited patents are not adapted for the solution of this different problem — all being designed, rather, to be used after non-stylet-type needles have completed their task and are ready for safe disposal or with stylet-type needles to be discarded.

While synergism affords the stylet-sticking safeguard structure of the present invention a supplementary benefit of enabling indication of the depth of insertion of the needle, if desired, such is not to be confused with the myriad of mere prior depth gauges that have been proposed (as, for example, in U.S. Pat. Nos. 4,378,810 and 4,142,517, or the type KNDM-160000 plastic sleeve of Cook Company, the grommet of the In Rad DLP Inc. "Accumark Sheath", or disc of Monoject "ABC" needle, or "AIM" movable marker of Medi-Tech) which are incapable of serving the stylet wound-prevention primary function of the present invention.

An object of the present invention, accordingly, is to provide a new and improved method of surgical use of needle-stylet assemblies, and an improved needle-stylet apparatus that obviate the dangers of wounding the operator's fingers during repeated reinsertion of the stylet into the needle as it probes for the desired precise location in the body from which to aspirate fluids or tissue or to which to apply treatment through the needle.

A further object is to provide a novel combined needle-stylet finger guard or shield structure which is also adapted simultaneously to provide an indication of and guide for needle insertion depth, as well.

Other and further objects will be explained hereinafter and are more particularly delineated in the appended claims.

In summary, however, from one of its viewpoints, the invention embraces a surgical method of needle probing for a predetermined location in the body from which either to aspirate or withdraw fluid or tissue or to which to deliver fluid, air or other materials, that comprises, occluding the cylindrical longitudinally extending needle lumen by inserting into the needle proximal end opening a longitudinal stylet extending coaxially through the lumen to block the distal needle end insertion opening; attaching around the external circumference of the needle at a predetermined position thereof an outwardly extending shielding surface of lateral width sufficient substantially to cover the thumb and forefinger of one hand of an operator holding the needle in a region between the shielding surface and the body; inserting the needle into the body to a depth estimated to reach the desired location; withdrawing the stylet through said needle proximal end to open the needle lumen; ascertaining whether the needle has reached the desired location and in the event of error in such depth estimation or the failure to reach the desired location, reinserting with the other hand of the operator said stylet back into the needle proximal end opening to re-occlude the needle lumen while guarding the thumb and forefinger of said one hand by said shielding surface against accidental sticking by the stylet during such reinsertion; changing the depth or position of reinsertion of the stylet-re-occluded needle to try again to reach the said desired location; repeating the stylet withdrawing and location ascertaining steps; and, upon ascertaining that the location of the needle distal end is at the desired location, conducting one or more of the fluid aspirating, tissue withdrawing or fluid, air or other material delivery steps. Preferred and best mode embodiments, including the novel needle-stylet apparatus for carrying out the method underlying the invention, are later presented in detail.

The invention will now be described with reference to the accompanying drawings, FIG. 1 of which is a side elevation of a conventional needle-stylet assembly to which has been combined an adjustable shielding or guard surface in accordance with the present invention;

Figure 4:
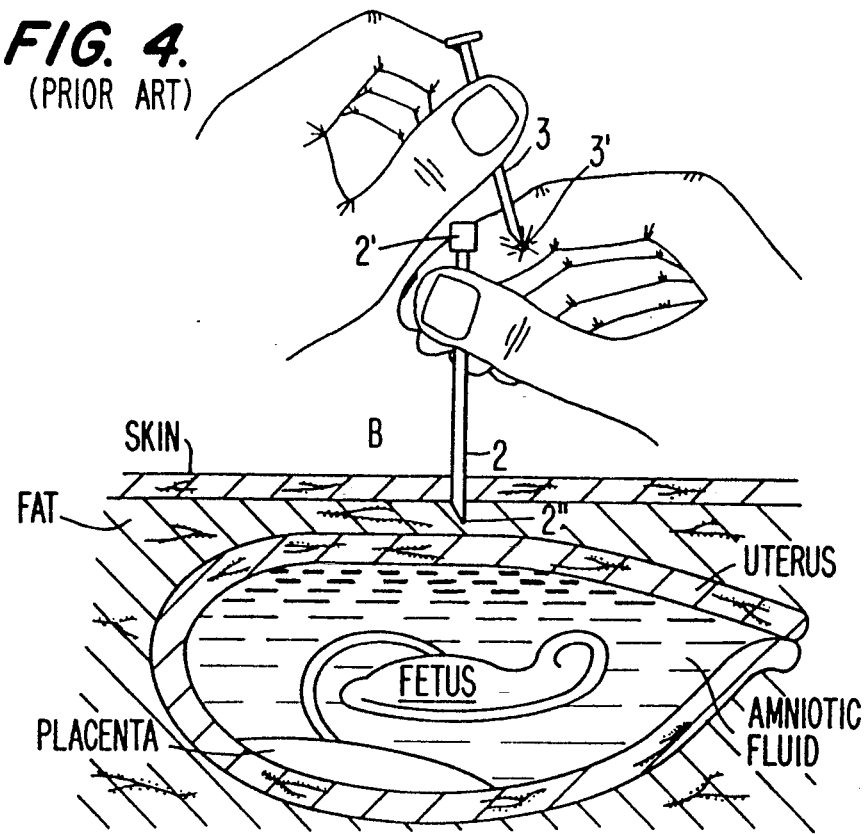
Figure 5:
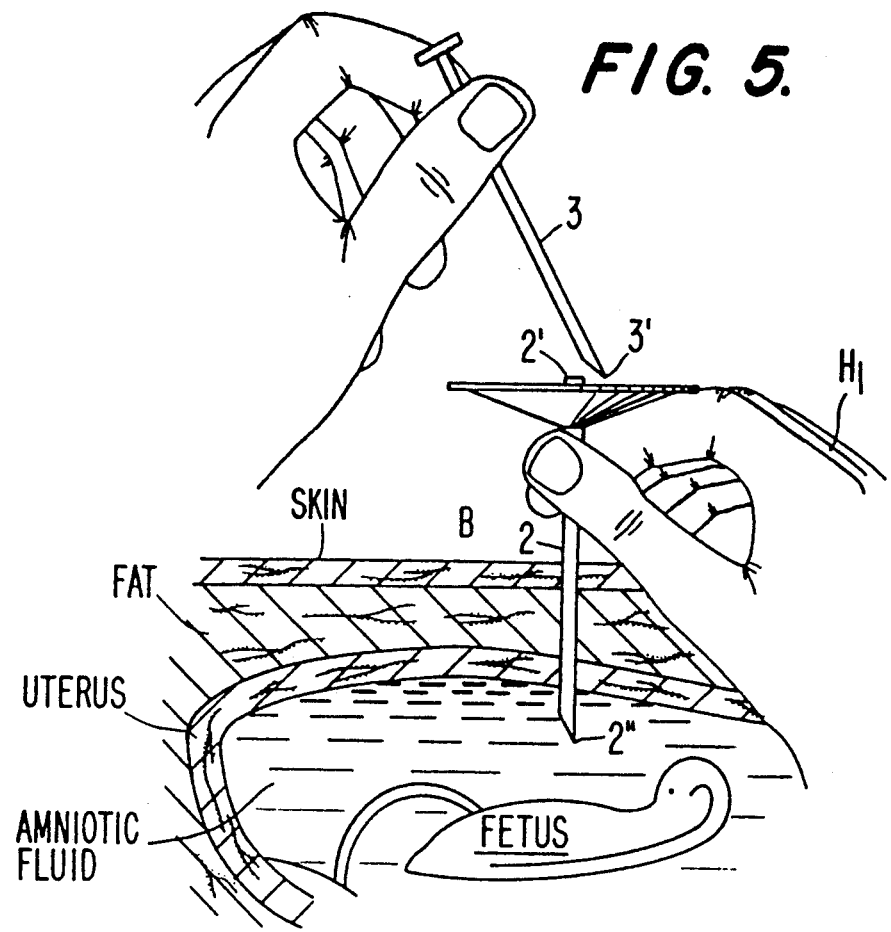
Figure 6:
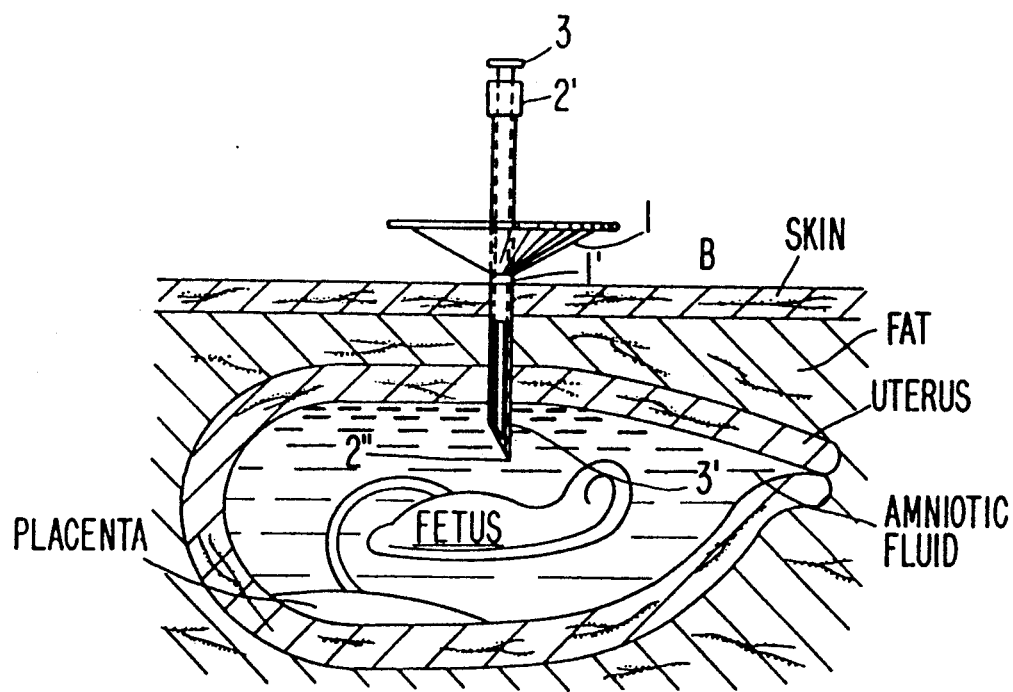
Figure 7:
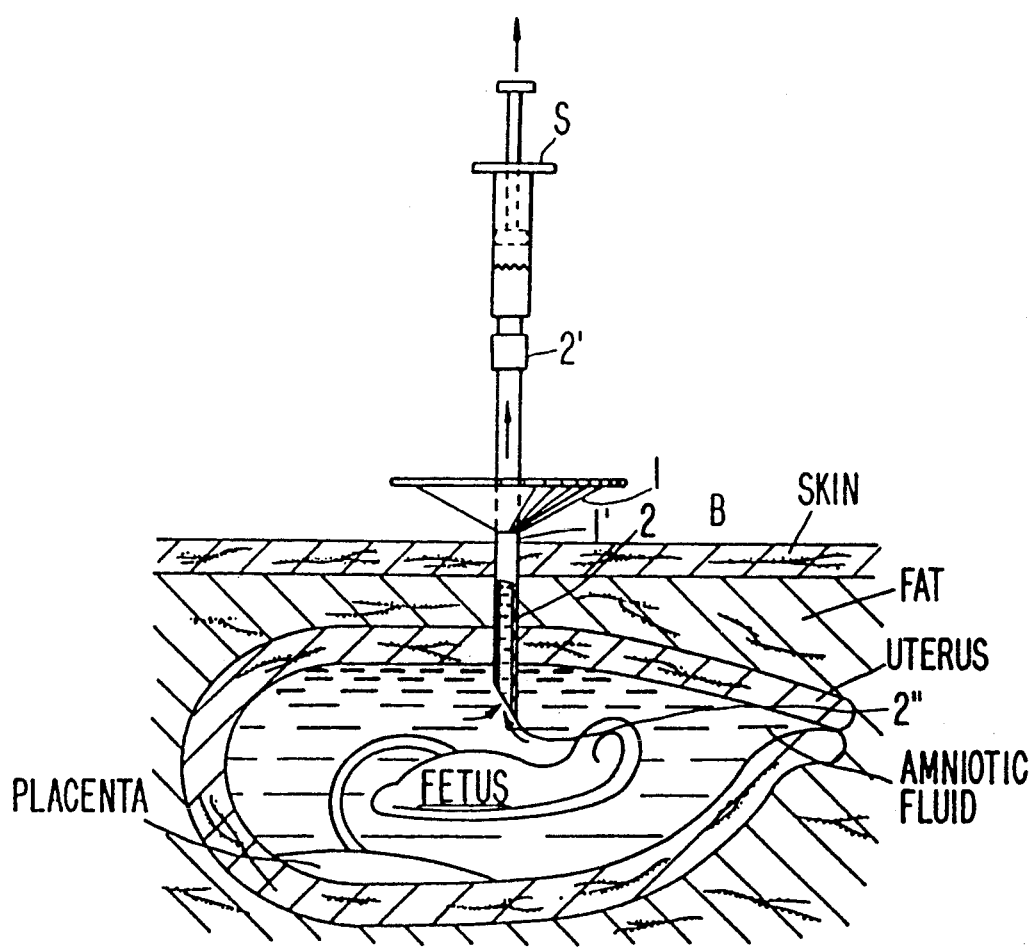

FIG. 4 is a similar view, also upon an enlarged scale, illustrating the required replacement of the stylet in an apparatus unequipped with the invention in the circumstance where the needle has not been inserted sufficiently to reach, for example, the amniotic fluid that it is desired to sample, and must be occluded by the reinsertion of the stylet before being further inserted, this figure demonstrating the stylet finger-puncturing danger;

FIG. 5 is a view similar to FIG. 4 but employing the shielding and guarding advantage of the invention during reinsertion of the stylet;

FIG. 6 shows the stylet re-occluding the needle so that the same may be advanced further through the uterus into the desired location of the amniotic fluid; and FIG. 7 shows the needle finally in the correct location in the amniotic fluid for syringe withdrawal of a sample of the same, and with the shielding surface also acting as the correct depth monitor.

Figure 1:
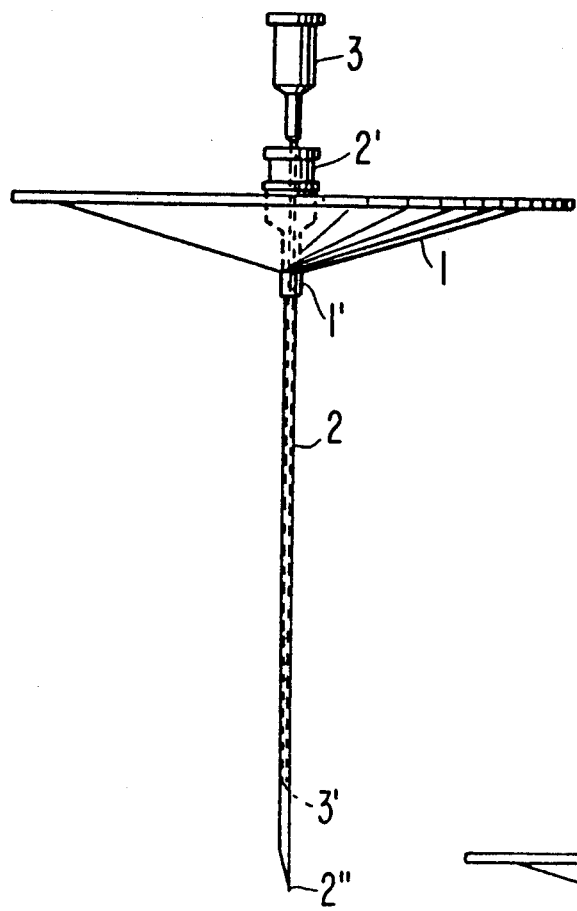
Figure 2:
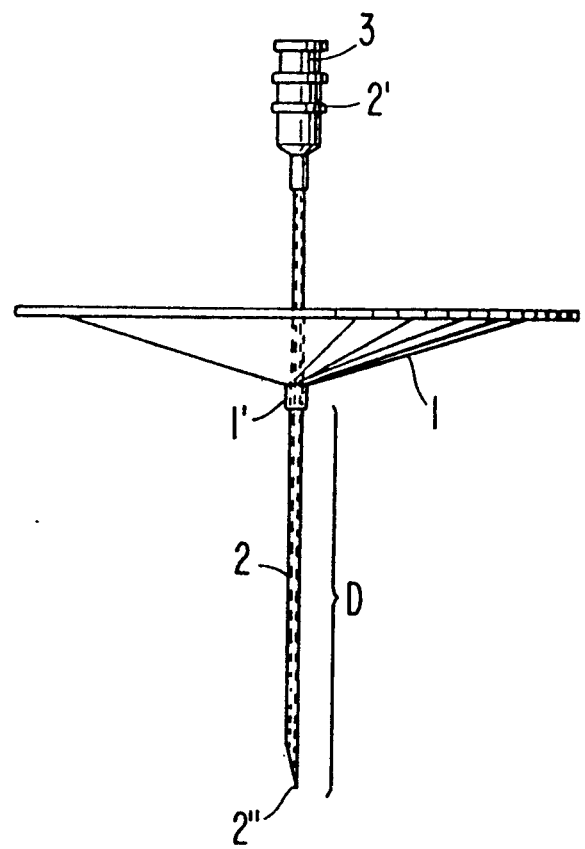
FIG. 2 is a view similar to FIG. 1 illustrating a typical positioning of the shielding surface, FIG. 1 showing the partial withdrawal of the stylet from the needle.

Referring to FIGS. 1 and 2, a shielding or guard surface 1, such as a rigid, puncture-proof conical funnel as of plastic of the like provided with a sleeve 1' at its apex for receiving the needle shank or shaft 2, is shown preferably slidably attached and longitudinally positionable along the needle between the proximal end hub 2' and the pointed insertion distal end 2". The before-mentioned needle-lumen-occluding stylet is shown at 3, with its lower tip 3' just slightly raised in FIG. 1 to open the distal insertion end 2" of the needle which it otherwise blocks when fully inserted into the needle. Such blocking or occluding is the prerequisite of inserting the needle into the body to probe toward the desired location therein, with the stylet withdrawal then being effected to permit aspiration or fluid application or other functions, as before explained, through the open needle.

In FIG. 1, the shielding or guard surface is positioned just under the hub 2'. By employing a resilient friction-fitting sleeve 1', as of plastic, rubber or the like, the guard 1 may be adjustably slid or positioned along the needle shank and held snugly in such position, also accommodating a range of different gauge needles. Thus in FIG. 2, the shielding guard funnel 1 has been positioned lower on the needle shank 2 at a distance D from the needle distal insertion end 2" that might correspond to any desired depth corresponding to the selected depth of insertion into the body. The snug friction fit of the sleeve 1' on the needle external surface allows ready variable positioning with infinite adjustments before, during or after needle insertion. As shown, the shielding surface 1 extends laterally outward around the external circumference of the needle 2 and, as later more fully evident from the embodiment of FIG. 5, is designed to be of lateral diameter (or, more generally, width) sufficient substantially to cover the thumb and forefinger of that hand $H_1$ of the operator that holds the needle in the region between the shielding surface 1 and the body B.

As before mentioned, the approximate depth of the desired location in the body may be initially ascertained by ultrasound, X-ray, CAT scan or other imaging or related techniques; but in actual practice, it may take several probing tries to reach the precise desired location with the needle; or, once reached, then to proceed to other depths or locations. This necessitates re-insertion of the stylet into the needle as previously discussed with the serious danger (without the present invention) illustrated in FIG. 4, of puncturing or sticking the forefinger of the hand $H_1$.

Figure 3:
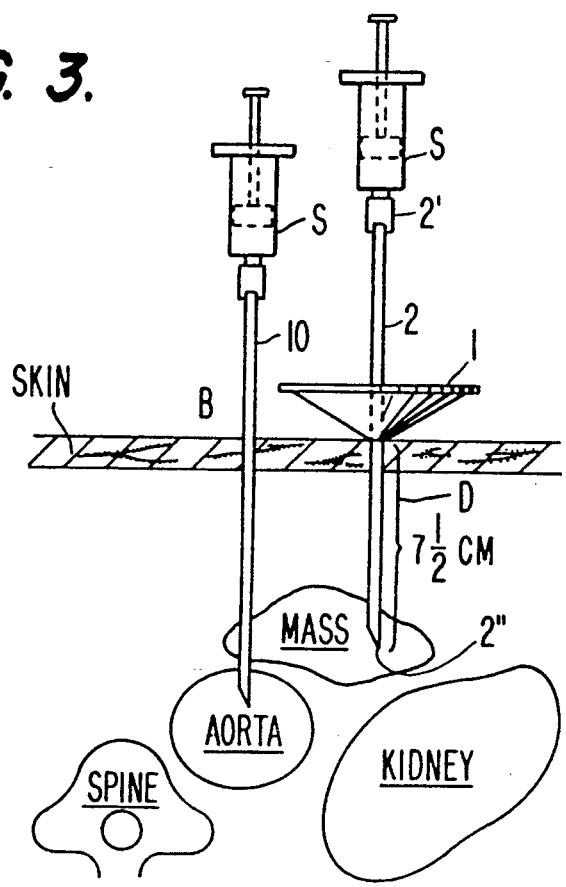
FIG. 3 is a view similar to FIG. 2 upon an enlarged scale, illustrating an exemplary use of the needle seeking a desired mass in the human body, with and without the aid of the invention and with a syringe attached to the open needle.

In FIG. 3, the concomitant dangers of needle probing into the body are illustrated. The left-hand needle 10, to which a syringe S has been attached after the needle insertion into the body B, has penetrated too deeply — through the desired "MASS" from which, for example, a fluid or tissue sample is to be aspirated or withdrawn through the needle by the syringe S, and into the "AORTA". The right-hand use of the present invention demonstrates the depth monitoring, indicating and guiding function of the shield 1, pre-positioned at depth D, which may be aided by calibrations on the needle shank. The sleeve 1' will abut the skin of the body B and stop the needle 2 from penetrating too deeply into the MASS and perhaps puncturing the KIDNEY. This function, as heretofore stated, is supplementary to the guarding against finger puncture when the syringe is removed and the stylet re-inserted for further adjustment of the needle. The ready re-adjustment of the shield 1 upward during such re-insertion, as in the illustration of FIG. 5, enables the primary hand-protection feature of the invention to be achieved.

Whether the needle has indeed reached the desired location in the body may be ascertained or monitored in various ways. Sometimes mere visual inspection after removal of the stylet may aid; and sometimes the failure of fluid or tissue withdrawal by the syringe attached to the needle hub will indicate error in or improper location. Such, indeed, could be the situation in FIG. 4, where the needle distal end 2" has penetrated the skin but not the uterus and has not reached the amniotic fluid which it is desired to aspirate. In FIG. 6, the needle has been re-occluded by the reinsertion of the stylet 3 while the needle is still in situ in the body, and advanced into the amniotic fluid. Attachment of the syringe S, FIG. 7, after removal of the stylet, with the shield 1 moved to abut the skin and delimit further penetration of the needle, will enable aspiration or suction of the desired fluid sample through the open needle bore into the syringe for laboratory analysis.

The invention, accordingly, provides for both the safety of periodic stylet withdrawal and re-insertion and the safety of needle depth penetration limitations with a common simple and disposable apparatus. The surgical technique or method of use is readily complimentary to present-day needle-stylet use with negligible instruction or explanation required.

Other advantages of this product over current art are that it is inexpensive, easily sterilized, has no moving parts, is lightweight and unobtrusive. It is designed to prevent needle stick injuries during the performance of a common procedure in which the stylet-type needle is placed under asceptic conditions into a predetermined body space and it can also serve simultaneously as a depth gauge to prevent inadvertent placement of the needle deeper than desired, thus preventing injury to structures below the desired depth as previously set forth. It can be repositioned easily during the procedure by simply pushing it to the desired depth.

Alternatively, the shielding guard 1 may also be fixed to instead of adjustable along the needle, preferably, though not essentially, positioned just below the hub 1', as in the position of FIG. 1.

In the preferred form shown, as before discussed, the device is funnel-shaped with a radially extending flange and a central vertex sleeve 1' where the structure converges toward the needle that is sized to friction-fit to the desired diameter of the needle. It is preferably constructed of a puncture-proof, sterilizable rigid, puncture-proof material and may be discarded with the needle after use.

In practice, the flanged cone guard 1 may be of the order of one cm. in height and about 3-4 cms. in diameter or lateral width, such protecting the forefinger and thumb areas. The top of the cone is shown truncated in the drawings, and the sleeve 1' may be a 6 mm hollow tube molded into the form to ensure rigid placement on the needle. The needle fits through the aperture of this tube, as earlier explained, with a movable friction fit to allow adjustability.

While the invention has primarily been described in connection with fluid or tissue aspiration or withdrawal, as before stated, medication or other materials may also be injected or other treatment applied as is well known. Though the shield or guard is shown in its preferred conical funnel form, enabling a narrow apex sleeve adjustment and depth indicating region, while the upwardly flared shielding surface is of sufficient lateral width to provide finger protection, other guard geometries may also be employed without departing from the inventive concept herein. If depth guarding is otherwise provided or not desired, moreover, the stylet shielding function alone may be employed. While the flexible friction-fit technique for holding the shielding guard in position on the needle shank is preferred, other well-known securing or clamping techniques may also be used. As before stated, the guard may also be fixed and not adjustable along the needle, if desired. Further modifications will also occur to those skilled in this art, and such are considered to fall within the spirit and scope of the invention as defined in the appended claims.

What is claimed is:

1. Surgical needle probing and aspiration having, in combination, an outer hollow needle provided with a bore extending from a proximal hub end to a distal insertion end, an inner removable stylet extending coaxially along the bore from the hub end to the insertion end of the needle, and shielding guard means intermediately apertured to receive the needle-stylet and provided with means for positioning the same at a predetermined position along the needle below the said proximal hub end of the needle, the guard means extending laterally of the external circumferential surface of the needle and around the needle sufficiently to protect the fingers of one hand holding the needle between the guard means and the said distal intertion end of the needle from contact with the stylet during its re-insertion by the other hand, following removal, into the said hub end of the needle, and in which means is provided for varying the said position of the guard means along the needle to control or limit the depth of penetration of the needle into the body and in which said guard means comprises means converging toward the needle and there-provided with sleeve means slidable along the needle for adjusting the position of the guard means therealong, and in which said guard means is conical.

2. Surgical needle probing and aspiration apparatus having, in combination, an outer hollow needle provided with a bore extending from a proximal hub end to a distal insertion end, an inner removable stylet extending coaxially along the bore from the hub end to the insertion end of the needle, and shielding guard means intermediately apertured to receive the needle-stylet and provided with means for positioning the same at a predetermined position along the needle below the said proximal hub end of the needle, the guard means extending laterally of the external circumferential surface of the needle and around the needle sufficiently to protect the fingers of one hand holding the needle between the guard means and the said distal insertion end of the needle from contact with the stylet during its re-insertion by the other hand, following removal, into the said hub end of the needle, and in which means is provided for varying the said position of the guard means along the needle to control or limit the depth of penetration of the needle into the body and in which said guard means comprises means converging toward the needle and the re-provided with sleeve means slidable along the needle for adjusting the position of the guard means therealong and in which said sleeve means comprises a sleeve frictionally holding the same to the needle.

* * * * *